US009149193B2

(12) United States Patent
Wolinsky et al.

(10) Patent No.: US 9,149,193 B2
(45) Date of Patent: Oct. 6, 2015

(54) DEVICES FOR FIXING A SENSOR IN A LUMEN

(75) Inventors: Lone Wolinsky, Ramat Gan (IL); Alon Ben-Yoseph, Amek Yisrael (IL); Abraham Penner, Tel Aviv (IL)

(73) Assignee: Remon Medical Technologies LTD, Caesarea (IL)

( * ) Notice: Subject to any disclaimer, the term of this patent is extended or adjusted under 35 U.S.C. 154(b) by 275 days.

(21) Appl. No.: 12/496,904

(22) Filed: Jul. 2, 2009

(65) Prior Publication Data
US 2009/0270742 A1 Oct. 29, 2009

Related U.S. Application Data

(63) Continuation of application No. 11/034,502, filed on Jan. 12, 2005, now Pat. No. 7,572,228.

(60) Provisional application No. 60/536,580, filed on Jan. 13, 2004.

(51) Int. Cl.
| | | |
|---|---|---|
| A61B 5/02 | (2006.01) | |
| A61B 5/0215 | (2006.01) | |
| A61B 5/00 | (2006.01) | |
| A61F 2/86 | (2013.01) | |
| A61B 5/145 | (2006.01) | |
| A61F 2/82 | (2013.01) | |

(52) U.S. Cl.
CPC ............ *A61B 5/0215* (2013.01); *A61B 5/0031* (2013.01); *A61B 5/6882* (2013.01); *A61B 5/6886* (2013.01); *A61F 2/86* (2013.01); *A61B 5/145* (2013.01); *A61F 2/82* (2013.01); *A61F 2230/0091* (2013.01); *A61F 2250/0002* (2013.01)

(58) Field of Classification Search
CPC .............................. A61B 5/021; A61B 5/0215
USPC .................................. 600/481, 485–488, 547
See application file for complete search history.

(56) References Cited

U.S. PATENT DOCUMENTS

| | | | |
|---|---|---|---|
| 3,874,388 | A | 4/1975 | King et al. |
| 4,391,124 | A | 7/1983 | Drost et al. |
| 4,407,296 | A | 10/1983 | Anderson |
| 4,485,813 | A | 12/1984 | Anderson et al. |
| 4,492,107 | A | 1/1985 | Sandhu |

(Continued)

FOREIGN PATENT DOCUMENTS

| | | |
|---|---|---|
| EP | 0897690 | 2/1999 |
| EP | 0928598 | 8/2000 |

(Continued)

OTHER PUBLICATIONS

Holmes et al. "SirolimusEluting Stents vs. Vascular Brachytherapy for InStent Restenosis Within BareMetal Stents" JAMA295 (11): 1264-1273 Mar. 15, 2006.

(Continued)

*Primary Examiner* — Michael D'Angelo
(74) *Attorney, Agent, or Firm* — Faegre Baker Daniels LLP (57) ABSTRACT

Apparatus for positioning at least one sensor in a body lumen, the apparatus including a fixation element, a sensor, and a connecting element that connects the sensor to the fixation element, the connecting element extending at least partially into the lumen so that the sensor is located radially inward from a wall of the lumen.

19 Claims, 4 Drawing Sheets

(56) References Cited

U.S. PATENT DOCUMENTS

| | | |
|---|---|---|
| 4,672,976 A | 6/1987 | Kroll |
| 4,836,204 A | 6/1989 | Landymore et al. |
| 4,846,191 A | 7/1989 | Brockway et al. |
| 4,886,065 A | 12/1989 | Collings, Jr. |
| 4,900,303 A | 2/1990 | Lemelson |
| 4,917,089 A | 4/1990 | Sideris |
| 4,966,148 A | 10/1990 | Millar |
| 5,040,538 A | 8/1991 | Mortazavi |
| 5,218,965 A | 6/1993 | Ring |
| 5,284,138 A | 2/1994 | Kujawski |
| 5,303,207 A | 4/1994 | Brady et al. |
| 5,334,217 A | 8/1994 | Das |
| 5,411,551 A | 5/1995 | Winston et al. |
| 5,415,630 A | 5/1995 | Gory et al. |
| 5,451,235 A | 9/1995 | Lock et al. |
| 5,509,900 A * | 4/1996 | Kirkman ............ 604/104 |
| 5,604,531 A | 2/1997 | Iddan et al. |
| 5,634,936 A | 6/1997 | Linden et al. |
| 5,656,036 A | 8/1997 | Palmaz |
| 5,662,711 A | 9/1997 | Douglas |
| 5,704,352 A | 1/1998 | Tremblay et al. |
| 5,725,552 A | 3/1998 | Kotula et al. |
| 5,733,249 A | 3/1998 | Katzin et al. |
| 5,733,294 A * | 3/1998 | Forber et al. ............ 606/151 |
| 5,733,313 A | 3/1998 | Barreras, Sr. et al. |
| 5,772,669 A | 6/1998 | Vrba |
| 5,775,331 A | 7/1998 | Raymond et al. |
| 5,800,497 A | 9/1998 | Bakels et al. |
| 5,824,053 A * | 10/1998 | Khosravi et al. ............ 623/1.15 |
| 5,833,603 A | 11/1998 | Kovacs et al. |
| 5,855,563 A | 1/1999 | Kaplan et al. |
| 5,860,923 A | 1/1999 | Lenker et al. |
| 5,891,154 A | 4/1999 | Loeffler |
| 5,967,980 A | 10/1999 | Ferre et al. |
| 5,967,986 A | 10/1999 | Cimochowski et al. |
| 5,967,989 A | 10/1999 | Cimochowski et al. |
| 5,995,876 A | 11/1999 | Kruse et al. |
| 6,002,969 A | 12/1999 | Machek et al. |
| 6,015,386 A | 1/2000 | Kensey et al. |
| 6,015,387 A | 1/2000 | Schwartz et al. |
| 6,030,413 A | 2/2000 | Lazarus |
| 6,033,366 A | 3/2000 | Brockway et al. |
| 6,053,873 A * | 4/2000 | Govari et al. ............ 600/505 |
| 6,076,016 A | 6/2000 | Feierbach |
| 6,077,227 A | 6/2000 | Miesel et al. |
| 6,097,984 A | 8/2000 | Douglas |
| 6,106,464 A | 8/2000 | Bass et al. |
| 6,140,740 A | 10/2000 | Porat et al. |
| 6,159,156 A | 12/2000 | Van Bockel |
| 6,179,858 B1 | 1/2001 | Squire et al. |
| 6,193,745 B1 | 2/2001 | Fogarty et al. |
| 6,214,025 B1 | 4/2001 | Thistle et al. |
| 6,231,516 B1 | 5/2001 | Keilman et al. |
| 6,236,889 B1 | 5/2001 | Soykan et al. |
| 6,239,724 B1 | 5/2001 | Doron et al. |
| 6,240,312 B1 | 5/2001 | Alfano et al. |
| 6,246,898 B1 | 6/2001 | Vesely et al. |
| 6,277,078 B1 | 8/2001 | Porat et al. |
| 6,278,790 B1 | 8/2001 | Davis et al. |
| 6,309,350 B1 | 10/2001 | Van Tassel |
| 6,328,669 B1 | 12/2001 | Imanishi et al. |
| 6,328,699 B1 | 12/2001 | Eigler et al. |
| 6,331,163 B1 | 12/2001 | Kaplan |
| 6,379,308 B1 | 4/2002 | Brockway et al. |
| 6,409,674 B1 | 6/2002 | Brockway et al. |
| 6,416,474 B1 | 7/2002 | Penner et al. |
| 6,432,050 B1 | 8/2002 | Porat et al. |
| 6,442,413 B1 | 8/2002 | Silver |
| 6,447,522 B2 | 9/2002 | Gambale et al. |
| 6,475,170 B1 | 11/2002 | Doron et al. |
| 6,486,588 B2 | 11/2002 | Doron et al. |
| 6,527,780 B1 | 3/2003 | Wallace et al. |
| 6,543,272 B1 | 4/2003 | Vitek |
| 6,585,763 B1 | 7/2003 | Keilman et al. |
| 6,592,553 B2 | 7/2003 | Zhang et al. |
| 6,628,989 B1 | 9/2003 | Penner et al. |
| 6,645,143 B2 | 11/2003 | Van Tassel et al. |
| 6,660,021 B1 | 12/2003 | Palmer et al. |
| 6,685,638 B1 | 2/2004 | Taylor et al. |
| 6,699,186 B1 | 3/2004 | Wolinsky et al. |
| 6,702,847 B2 | 3/2004 | DiCarlo |
| 6,730,108 B2 | 5/2004 | Van Tassel et al. |
| 6,738,671 B2 | 5/2004 | Christophersom et al. |
| 6,743,173 B2 | 6/2004 | Penner et al. |
| 6,746,404 B2 | 6/2004 | Schwartz |
| 6,747,916 B1 | 6/2004 | Fleury et al. |
| 6,755,855 B2 | 6/2004 | Yurek et al. |
| 6,764,446 B2 | 7/2004 | Wolinsky et al. |
| 6,783,499 B2 | 8/2004 | Schwartz |
| 6,800,060 B2 | 10/2004 | Marshall |
| 6,840,956 B1 | 1/2005 | Wolinsky et al. |
| 6,855,115 B2 | 2/2005 | Fonseca et al. |
| 6,868,288 B2 | 3/2005 | Thompson |
| 6,890,303 B2 | 5/2005 | Fitz |
| 6,899,729 B1 | 5/2005 | Cox et al. |
| 6,904,308 B2 | 6/2005 | Frisch et al. |
| 6,920,347 B2 | 7/2005 | Simon et al. |
| 6,926,670 B2 | 8/2005 | Rich |
| 6,934,573 B1 | 8/2005 | Glukhovsky et al. |
| 6,950,690 B1 | 9/2005 | Meron et al. |
| 6,958,034 B2 | 10/2005 | Iddan |
| 6,970,742 B2 | 11/2005 | Mann et al. |
| 6,972,017 B2 | 12/2005 | Smith et al. |
| 6,984,205 B2 | 1/2006 | Gazdzinski |
| 7,001,329 B2 | 2/2006 | Kobayashi et al. |
| 7,006,858 B2 | 2/2006 | Silver et al. |
| 7,009,634 B2 | 3/2006 | Iddan et al. |
| 7,011,671 B2 | 3/2006 | Welch |
| 7,024,248 B2 | 4/2006 | Penner et al. |
| 7,033,322 B2 | 4/2006 | Silver |
| 7,035,684 B2 | 4/2006 | Lee |
| 7,039,453 B2 | 5/2006 | Mullick et al. |
| 7,060,038 B2 | 6/2006 | Letort et al. |
| 7,064,472 B2 | 6/2006 | Peline et al. |
| 7,065,409 B2 | 6/2006 | Mazar |
| 7,065,709 B2 | 6/2006 | Ellis et al. |
| 7,083,822 B2 | 8/2006 | Brightbill |
| 7,116,352 B2 | 10/2006 | Yaron |
| 7,118,529 B2 | 10/2006 | Glukhovsky et al. |
| 7,118,531 B2 | 10/2006 | Krill |
| 7,131,986 B2 | 11/2006 | Sirhan et al. |
| 7,160,258 B2 | 1/2007 | Imran et al. |
| 7,181,261 B2 | 2/2007 | Silver et al. |
| 7,198,603 B2 | 4/2007 | Penner et al. |
| 7,211,045 B2 | 5/2007 | Dala-Krishna et al. |
| 7,273,457 B2 | 9/2007 | Penner |
| 7,283,874 B2 | 10/2007 | Penner |
| 7,308,319 B2 | 12/2007 | Lovett et al. |
| 7,338,512 B2 | 3/2008 | McGuckin, Jr. et al. |
| 7,347,868 B2 | 3/2008 | Burnett et al. |
| 7,392,094 B2 | 6/2008 | Zhang et al. |
| 7,437,193 B2 | 10/2008 | Parramon et al. |
| 7,452,334 B2 | 11/2008 | Gianchandani et al. |
| 7,477,946 B2 | 1/2009 | Tockman et al. |
| 7,555,351 B2 | 6/2009 | Zhang et al. |
| 7,780,694 B2 | 8/2010 | Palmer et al. |
| 7,850,708 B2 | 12/2010 | Pal |
| 7,890,188 B2 | 2/2011 | Zhang et al. |
| 9,026,229 B2 | 5/2015 | Stalker et al. |
| 2002/0077555 A1* | 6/2002 | Schwartz ............ 600/486 |
| 2002/0123672 A1 | 9/2002 | Christophersom et al. |
| 2002/0151816 A1* | 10/2002 | Rich et al. ............ 600/547 |
| 2002/0165601 A1 | 11/2002 | Clerc |
| 2002/0183628 A1 | 12/2002 | Reich et al. |
| 2002/0188207 A1 | 12/2002 | Richter |
| 2003/0114897 A1 | 6/2003 | Von Arx et al. |
| 2003/0139796 A1 | 7/2003 | Sequin et al. |
| 2003/0195606 A1 | 10/2003 | Davidson et al. |
| 2003/0200031 A1 | 10/2003 | de Kok |
| 2004/0006377 A1 | 1/2004 | Behm |
| 2004/0054403 A1 | 3/2004 | Israel |
| 2004/0116992 A1* | 6/2004 | Wardle et al. ............ 607/116 |
| 2004/0147969 A1 | 7/2004 | Mann et al. |
| 2004/0176672 A1 | 9/2004 | Silver et al. |

(56) References Cited

U.S. PATENT DOCUMENTS

| | | |
|---|---|---|
| 2004/0204744 A1 | 10/2004 | Penner et al. |
| 2004/0215228 A1 | 10/2004 | Simpson et al. |
| 2005/0080472 A1 | 4/2005 | Atkinson et al. |
| 2005/0096702 A1 | 5/2005 | Denker et al. |
| 2005/0115561 A1 | 6/2005 | Stahmann et al. |
| 2005/0124875 A1 | 6/2005 | Kawano et al. |
| 2005/0136385 A1 | 6/2005 | Mann et al. |
| 2005/0149108 A1 | 7/2005 | Cox |
| 2005/0149128 A1 | 7/2005 | Heil, Jr. et al. |
| 2005/0149155 A1 | 7/2005 | Scheiner et al. |
| 2005/0149156 A1 | 7/2005 | Libbus et al. |
| 2005/0154321 A1 | 7/2005 | Wolinsky et al. |
| 2005/0165456 A1 | 7/2005 | Mann et al. |
| 2005/0182387 A1 | 8/2005 | Webler |
| 2005/0209678 A1 | 9/2005 | Henkes et al. |
| 2005/0245840 A1 | 11/2005 | Christopherson et al. |
| 2006/0009818 A1 | 1/2006 | Von Arx et al. |
| 2006/0047205 A1 | 3/2006 | Ludomirsky et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0079740 A1 | 4/2006 | Silver et al. |
| 2006/0089627 A1 | 4/2006 | Burnett et al. |
| 2006/0089694 A1 | 4/2006 | Zhang et al. |
| 2006/0122522 A1 | 6/2006 | Chavan et al. |
| 2006/0136004 A1 | 6/2006 | Cowan et al. |
| 2006/0142819 A1 | 6/2006 | Penner et al. |
| 2006/0149329 A1 | 7/2006 | Penner |
| 2006/0149330 A1 | 7/2006 | Mann et al. |
| 2006/0178586 A1 | 8/2006 | Dobak, III |
| 2006/0206153 A1 | 9/2006 | Libbus et al. |
| 2006/0241735 A1 | 10/2006 | Tockman et al. |
| 2006/0259085 A1 | 11/2006 | Zhang et al. |
| 2006/0287700 A1 | 12/2006 | White et al. |
| 2006/0293741 A1 | 12/2006 | Johnson et al. |
| 2007/0049833 A1 | 3/2007 | Tearney et al. |
| 2007/0060959 A1 | 3/2007 | Salo et al. |
| 2007/0129637 A1 | 6/2007 | Wolinsky et al. |
| 2007/0156126 A1 | 7/2007 | Flaherty |
| 2007/0156205 A1 | 7/2007 | Larson et al. |
| 2007/0162090 A1 | 7/2007 | Penner |
| 2007/0179583 A1 | 8/2007 | Goetzinger et al. |
| 2007/0191904 A1 | 8/2007 | Libbus et al. |
| 2007/0208390 A1 | 9/2007 | Von Arx et al. |
| 2007/0247565 A1 | 10/2007 | Sasiaki et al. |
| 2007/0250126 A1 | 10/2007 | Maile et al. |
| 2007/0274565 A1 | 11/2007 | Penner |
| 2007/0282413 A1 | 12/2007 | Tockman et al. |
| 2007/0282415 A1 | 12/2007 | Tockman et al. |
| 2008/0071178 A1 | 3/2008 | Greenland et al. |
| 2008/0071248 A1 | 3/2008 | Delgado et al. |
| 2008/0071339 A1 | 3/2008 | Stalker et al. |
| 2008/0108904 A1 | 5/2008 | Heil |
| 2008/0176271 A1 | 7/2008 | Silver et al. |
| 2008/0275350 A1 | 11/2008 | Liao et al. |
| 2008/0283066 A1 | 11/2008 | Delgado et al. |
| 2009/0054793 A1 | 2/2009 | Nunez et al. |
| 2009/0171274 A1 | 7/2009 | Harlev et al. |
| 2010/0016840 A1 | 1/2010 | Stahmann et al. |
| 2010/0210923 A1 | 8/2010 | Li et al. |

FOREIGN PATENT DOCUMENTS

| | | |
|---|---|---|
| EP | 1068836 | 1/2001 |
| EP | 1488735 | 6/2007 |
| GB | 2333044 | 7/1999 |
| JP | H(11)-089942 | 4/1999 |
| JP | 2000-507142 | 6/2000 |
| JP | 2001-061790 | 3/2001 |
| JP | 2006-500991 | 1/2006 |
| WO | WO 83/03348 | 10/1983 |
| WO | WO 99/34731 | 7/1999 |
| WO | WO 00/16686 | 3/2000 |
| WO | WO 00/59376 | 10/2000 |
| WO | WO 01/67989 | 9/2001 |
| WO | WO 01/87137 | 11/2001 |
| WO | WO 2004/024034 | 3/2004 |
| WO | WO 2004/110263 | 12/2004 |
| WO | WO 2005/058202 | 6/2005 |
| WO | WO 2005/066849 | 7/2005 |
| WO | WO 2005/067817 | 7/2005 |
| WO | WO 2006/062725 | 6/2006 |
| WO | WO 2007/057739 | 5/2007 |
| WO | WO 2007/062299 | 5/2007 |
| WO | WO 2007/082115 | 7/2007 |
| WO | 2008002654 | 1/2008 |
| WO | WO 2008/034077 | 3/2008 |
| WO | WO 2008/057720 | 5/2008 |
| WO | WO2008/060197 | 5/2008 |
| WO | WO 2008/144191 | 11/2008 |
| WO | 2009006610 | 1/2009 |

OTHER PUBLICATIONS

Lanning & Shandas, "Development and Validation of Implantable Sensors for Monitoring Function of Prosthetic Heart Valves: In Vitro Studies", Medical & Biological Engineering & Computing, Jul. 2003, vol. 41, issue 4, pp. 416-424.

Sheth et al. "Subacute Thrombosis and Vascular Injury Resulting From Slotted-Tube Nitinol and Stainless Steel Stents in a Rabbit Carotid Artery Model" Circulation 1996, 94: 1733-1740.

Stone et al. "Paclitaxel-Eluting Stents vs.Vascular Brachytherapy for In-Stent Restenosis Within Bare-Metal Stents" JAMA 295(11): 1253-1263, Mar. 15, 2006.

Wenaweser et al. "Stent thrombosis following baremetal stent implantation: success of emergency percutaneous coronary intervention and predictors of adverse outcome" European Heart Journal 26: 1180-1187 2005.

Goodall, Eleanor V. et al., "Position-Seletive Activation of Peripheral Nerve Fibers with a Cuff Electrode", IEEE Transactions on Biomedical Engineering, IEEE Service Center, Piscataway, NJ, US, vol. 43, No. 8, Aug. 1, 1996.

International Search Report and Written Opinion issued in PCT/US2010/020756, mailed Sep. 27, 2010.

Invitation to Pay Fees and Partial Search Report issued in PCT/US2010/020756, mailed May 12, 2010.

Mullins, C.E. et al., "Implantation of Balloon-Expandable Intravascular Grafts by Catheterization in Pulmonary Arteries and Systemic Veins", Circulation, 1988, vol. 77, pp. 188-199.

* cited by examiner

DEVICES FOR FIXING A SENSOR IN A LUMEN

CROSS-REFERENCE TO RELATED APPLICATION

This application is a continuation of U.S. patent application Ser. No. 11/034,502, filed on Jan. 12, 2005, which claims priority under 35 U.S.C. §119 to U.S. Provisional Patent Application Ser. No. 60/536,580, entitled "Device for Fixing a Sensor in a Lumen," filed on Jan. 13, 2004, each of which are expressly incorporated herein by reference in their entirety.

TECHNICAL FIELD

The present invention relates to field of medical devices and more specifically to a device for positioning a sensor in a lumen.

BACKGROUND

The use of sensors in body lumens is well known. For example, U.S. Pat. No. 4,485,813 describes a sensor that can be permanently implanted in a specific location within the human body in an implantable medical device such as a pacemaker. In other applications sensors are implanted alone in a body lumen. U.S. Pat. Nos. 6,645,143, 6,053,873, 6,442,413 and United States Publication Serial No. 2002/0188207 describe medical monitoring sensors designed to be implanted in the vascular system and are capable of sensing and transmitting via a telemetry link to an external monitor.

The implanted sensors are utilized for monitoring physical, chemical or physiological parameters in the body. The aim of such sensors is to accurately monitor the desired parameter.

The position of the sensor within the lumen can influence the accuracy of the measurement. Positioning of a sensor facing a lumen wall can alter the sensing ability. Furthermore, positioning of a sensor pressing against the lumen wall in blood vessels may encourage responses, such as neo-intimal growth, which can influence and/or impact the long and short term accuracy of measurements.

United States Publication Serial No. 2002/0188207 discloses a device and method for anchoring a sensor at the center of the lumen. This concept addresses the issue of tissue growth. However, it is problematic to axially align multiple sensors in the same vicinity of a lumen, since a first sensor would block the further sensor(s) from blood flow through the lumen. Thus, it is desirable, and often functionally necessary, to radially and/or circumferentially off-set the sensors of a multiple sensor arrangement, so that they are not coaxially aligned. On the other hand, it is desirable, and often functionally necessary, to operably connect the individual sensors of a multiple sensor arrangement.

There are several medical procedures that require insertion of catheters or other devices through a body lumen and especially through the vascular system, for example, Swan-Ganz catheter to the pulmonary artery for monitoring hemodynamic parameters. Thus, a sensor implantation device should not prevent accessibility to a desired location within the vascular system.

SUMMARY

One embodiment of the invention is an apparatus for positioning at least one sensor in a body lumen, the body lumen having a wall, the apparatus including a fixation element, a sensor, and a connecting element that connects the sensor to the fixation element. The connecting element extends at least partially into the lumen so that the sensor is located radially inward from the lumen wall. Other and further embodiments and aspects of the invention are disclosed and described herein.

BRIEF DESCRIPTION OF THE DRAWINGS

The present invention will be more fully understood and appreciated from the following detailed description taken in conjunction with the figures, in which.

DETAILED DESCRIPTION

The devices disclosed in the following detailed description enable positioning of an implant such as a sensor, a drug reservoir, or other known and/or convenient device within a lumen at a location which is between the inner lumen wall and the lumen center.

In one embodiment, the device includes a fixation part and an implant that is positioned between the lumen wall and the center of the lumen. The implant can be directly connected to the fixation part. The device can further include a connecting element for connecting between the fixation part and the implant and/or for positioning the implant at the desired location. The implant can be a sensor such as, for example, a pressure sensor that is implanted in blood vessels for monitoring blood pressure or any other known and/or convenient device. However, any known and/or convenient sensor can be used, including, but not limited to, a flow sensor, a radiation sensor, a temperature sensor, an electrical impedance sensor, other physical measurement sensor, an optical sensor for monitoring Hemoglobin concentrations and/or glucose, concentrations or any other measurement, or any type of sensor for monitoring chemical species and/or composition, and/or an electrochemical sensor for monitoring various compounds within the bloods, for example, calcium, potassium, sodium and/or any other measurable compound, molecule, atom, and/or ion.

In alternate embodiments, the device can further include a second implant located either in contact with the wall or at the vicinity of the wall or in any other convenient location within a lumen. The second implant can be a second sensor such as, for example, a flow sensor for monitoring flow in the cardiovascular system or an energy source such as a battery or any other known and/or convenient device. The second implant can be connected to the first implant. For example, a first implant which is a sensor can be electrically connected, using an isolated electric wire, to a second implant which is an energy source such as battery for enabling energy transfer from the energy source to the sensor.

In one embodiment, a first implant, which can be a sensor, can be located between the lumen wall and the center of the lumen and a second implant, which can be an energy source, can be located in contact with the lumen wall and electrically connected to the sensor. This configuration enables miniaturizing of the first implant since the energy source is not a part of the sensor.

The insertion of the device into a body lumen can be performed via a catheterization procedure. The device can be mounted on a delivery system, in a compressed configuration so as to enable navigation through the lumen, and delivered through the lumen to the desired deployment site. At the desired deployment site the expandable technique and/or any other known and/or convenient method and/or mechanism.

Other techniques for inserting a device into a lumen, such as making an incision in the lumen and suturing the device at the desired location can be applied. Additionally, the device can be connected to other implants.

Reference is now made to FIGS. 1A-1D illustrating a device that includes a fixation element having a stent-like configuration according to an embodiment of the invention. The devices shown in the embodiments include a fixation element 100, a connecting element 12 and a sensor 20. For convenience and clarity, the lumen 30 is shown in cross-section.

Figure 1A:
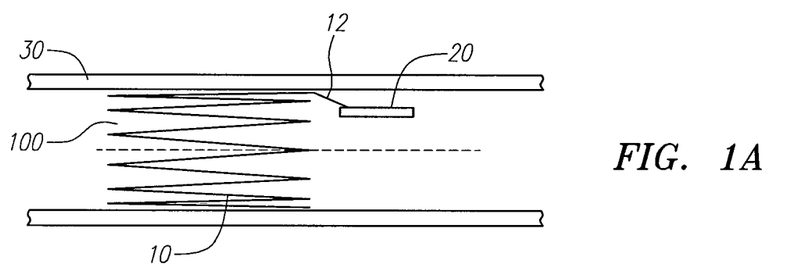
FIGS. 1A-1D are schematic illustrations of a device having a stent-like configured fixation element according to one an embodiment of the invention.

In the embodiment shown in FIG. 1A, fixation element 100 can be manufactured from a wire, a laser cut tube or a chemical etched tube or sheet made of metal, for example Nickel-Titanium alloy, stainless steel titanium, cobalt-based alloy, or a polymer including a shape memory polymer with or without the addition of radio-opaque material e.g. barium sulfate or can be manufactured from any known and/or convenient material using any known and/or convenient method and having any convenient shape. In the embodiment shown in FIG. 1A, the struts 10 cross section can be round, oval, rectangular or any convenient shape. In the embodiment shown in FIG. 1A, the struts are arranged in a zigzag configuration. However in alternate embodiments, the struts can have any convenient configuration. The thickness of struts 10 is in the range of 0.05-0.5 mm. However in alternate embodiments, various other thicknesses can be used. The struts can further include ridges or hooks for preventing migration within the lumen.

FIG. 1A shows fixation element 100 having a radial zigzag configuration that is in contact with the inner side of the lumen wall. The sensor 20 can be connected to a connecting element 12 for connecting sensor 20 to fixation element 100 and for positioning sensor 20 at a desired location distanced from the lumen wall. The sensor 20 can be located between the lumen wall and the center of the lumen. In some embodiments, the sensor can be distanced from the lumen wall between 0.05 mm and 0.8r wherein r is the lumen radius. For example, for a blood vessel having radius of r=10 mm the sensor can be positioned at a distance of 0.05 to 8 mm from the vessel wall.

In some embodiments, connecting element 12 can be made of metal such as Nickel-Titanium alloy, stainless steel, titanium, cobalt-based alloy, or using tantalum, gold, platinum or platinum-iridium for enhanced radio-opacity, or a polymer including a shape memory polymer with or without the addition of radio-opaque material e.g. barium sulfate, and/or composed of any known and/or convenient material and or made in any know and/or convenient shape using any known and/or convenient method.

Figure 1B:
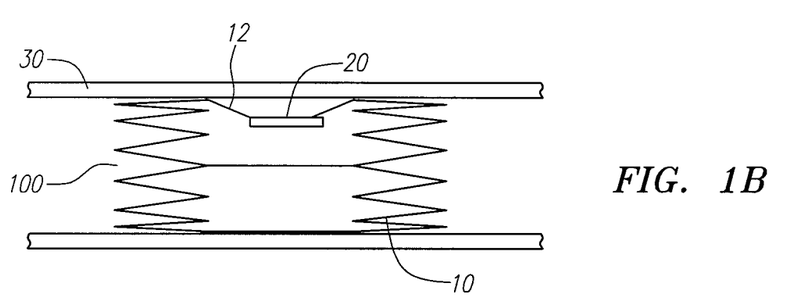
Figure 1C:
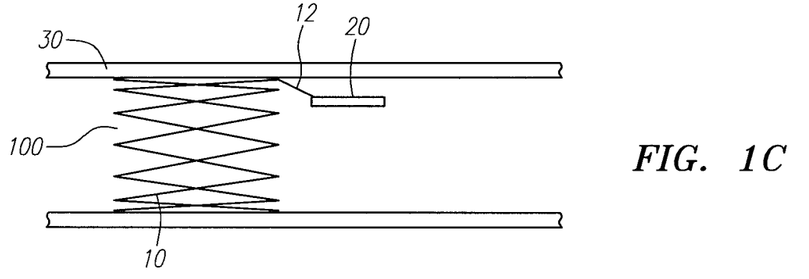
Figure 1D:
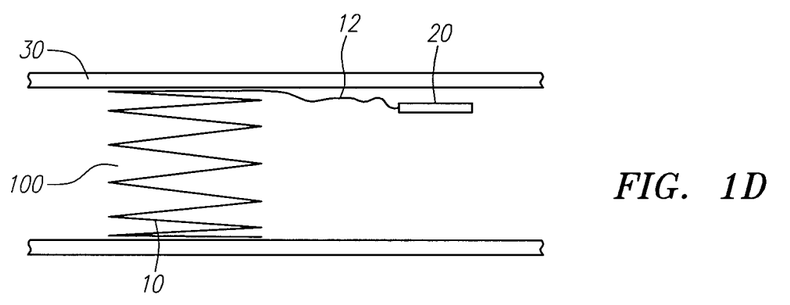

In some embodiments, connecting element 12 can be rigid so as to maintain sensor 20 at constant position or can be flexible as illustrated in FIG. 1D, so as to enable movement of the sensor within the lumen. In alternate embodiments, sensor 20 can be connected directly to strut 10 of fixation element 100. In selected embodiments, the sensor 20, can be located in a position proximal to the fixation element 100 to reduce neo intima and cell proliferation.

In alternate embodiments, sensor 20 can be oriented parallel, perpendicular or at any other angle to the lumen wall. In still further alternate embodiments, the active face of the sensor 20 can be oriented towards the lumen center, the lumen wall or tangential and/or in any other convenient location.

Reference is now made to FIG. 1B, illustrating one configuration of the device having two fixation elements 100 at both sides, proximal and distal to the sensor 20. In the embodiment shown in FIG. 1B, proximal and distal fixation elements 100 can be connected at one or more points and sensor 20 can be connected to fixation element 100 by one connecting element. That is, sensor 20 can be connected to the distal or proximal strut or can be connected to the distal and proximal strut. Sensor 20 can be oriented parallel, perpendicular or at any other angle to the lumen wall. The active face of the sensor 20 can be oriented towards the lumen center, the lumen wall or tangential or in any convenient orientation. In some embodiments, connecting element 12 can be rigid so as to maintain sensor 20 at constant position or can be flexible so as to allow movement of sensor 20.

Reference is now made to FIG. 1C, illustrating an alternate configuration of fixation element 100 in which the struts are configured in a closed cell zigzag arrangement. However in some embodiments, any known and/or convenient strut configuration can be used. Furthermore, it will be appreciated that other configurations can be used.

Figure 2A:
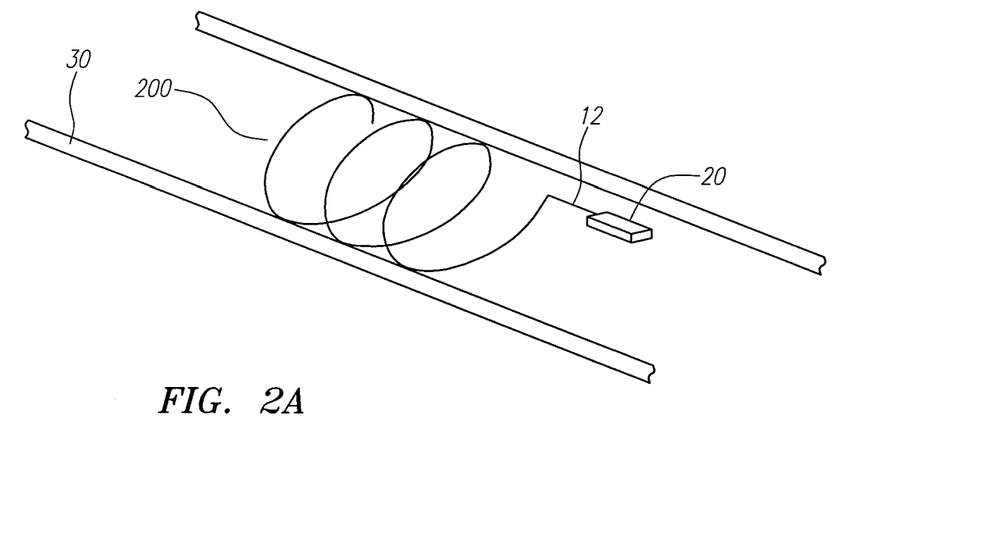
FIGS. 2A-2B are schematic illustrations of a device having a coiled configured fixation element according to another embodiment of the invention.
Figure 2B:
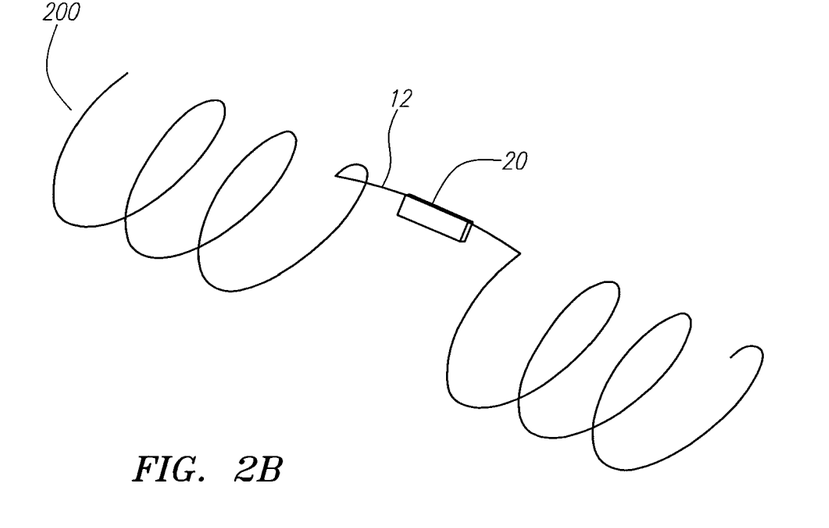

Reference is now made to FIGS. 2A-2B illustrating a device having a coiled fixation element 200 according to an embodiment of the invention. The device can include coiled configured fixation element 200, connecting element 12 and sensor 20. For clarity and convenience the lumen 30 is shown in cross-sectional view.

The coiled fixation element 200 can be manufactured from a wire, a laser cut tube or a chemical etched tube or sheet made of metal, for example Nickel-Titanium alloy, stainless steel titanium, cobalt-based alloy, or a polymer including a shape memory polymer with or without the addition of radio-opaque material e.g. barium sulfate or composed of any known and/or convenient material, in any convenient shape and/or using any known and/or convenient method. The fixation element cross-section may be round, oval, rectangular etc. The thickness of strut 10 of coiled fixation element 200 is in the range of 0.05-0.5 mm. Additionally in selected embodiments, the strut can further include ridges or hooks for preventing migration within the lumen.

The coiled fixation element 200 configuration can be radial and can be in contact with the lumen wall. The sensor 20 can be connected to a connecting element 12 for connecting sensor 20 to fixation element 200 and/or for positioning sensor 20 at a desired location distanced from the lumen wall. In alternate embodiments, sensor 20 can be connected directly to coil fixation element 200. In various embodiments, the sensor can be located between the lumen wall and the center of the lumen. In alternate embodiments the sensor can be distanced from the lumen wall between 0.05 mm and 0.8r wherein r is the lumen radius. However in alternate embodiments, the sensor can be located at any convenient distance from the lumen wall. For example, for blood vessel having radius of r=10 mm the sensor can be positioned at a distance of 0.05 to 8 mm of the vessel wall. In selected embodiments, connecting element 12 can be made of metal such as Nickel-Titanium alloy, stainless steel titanium, cobalt-based alloy, or using tantalum, gold, platinum or platinum-iridium for enhanced radio-opacity, or a polymer including a shape memory polymer with or without the addition of radio-opaque material e.g. barium sulfate, or any known and/or convenient material, in any convenient shape and manufactured in any known and/or convenient manner. In selected embodiments, connecting element 12 can be rigid so as to maintain sensor 20 at constant position or can be flexible so as to allow movement of sensor 20.

The sensor 20 may be oriented parallel, perpendicular or at any other angle to the lumen wall. The active face of the sensor 20 can be oriented towards the lumen center, the lumen wall, tangential to the lumen wall or at any other convenient angle within the lumen. In selected embodiments, sensor 20 can be oriented parallel, perpendicular or at any other angle to the lumen wall.

Reference is now made to FIG. 2B, illustrating a device having coiled fixation element 200 at both sides, of sensor 20. In the embodiment shown in FIG. 2B, proximal and distal coiled fixation element 200 can be connected at one or more points. Connecting element 12 can be rigid so as to maintain sensor 20 at constant position or can be flexible so as to allow movement of sensor 20. Additionally, sensor 20 can be oriented parallel, perpendicular or at any other angle to the lumen wall. The active face of the sensor 20 can be oriented towards the lumen center, the lumen wall or tangential. Furthermore, sensor 20 can be oriented parallel, perpendicular or at any other angle to the lumen wall. As will be apparent to those skilled in the art, other configurations can be used.

Reference is now made to FIGS. 3A-3D, illustrating a device having a wing-configured fixation element. In the embodiments shown in FIGS. 3A-3D, the device includes wing-configured fixation element 300, connecting element 12 and a sensor 20. For convenience and clarity, the lumen 30 is shown in cross-sectional view.

The wing-configured fixation element 300 may be manufactured from a wire, a laser cut tube or a chemical etched tube or sheet made of metal, for example Nickel-Titanium alloy, stainless steel titanium, cobalt-based alloy, or a polymer including a shape memory polymer with or without the addition of radio-opaque material, e.g. barium sulfate, or can be comprised of any known and/or convenient material, can be manufactured using any known and/or convenient shape and can be made using any known and/or convenient method.

The struts 10 of wing configured fixation element 300 may have a round, oval, rectangular etc. cross section. The thickness of struts 10 is in the range of 0.05-0.5 mm. The thickness of the struts may be any convenient thickness. Additionally, the struts can further include ridges or hooks for preventing migration within the lumen.

Figure 3A:
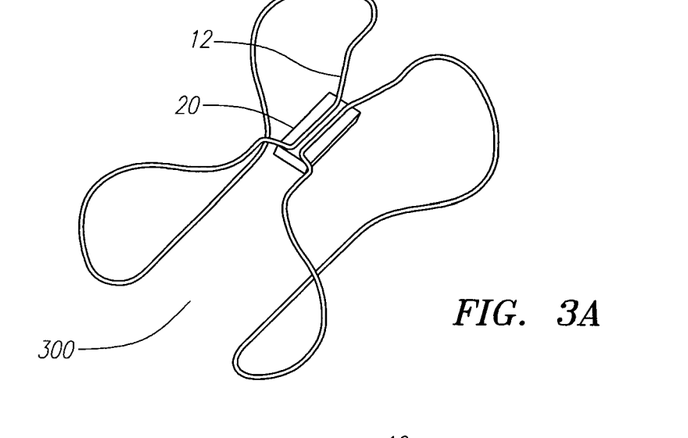
FIGS. 3A-3D are schematic illustrations of a device having a wing configured fixation element according to yet another embodiment of the invention.
Figure 3B:
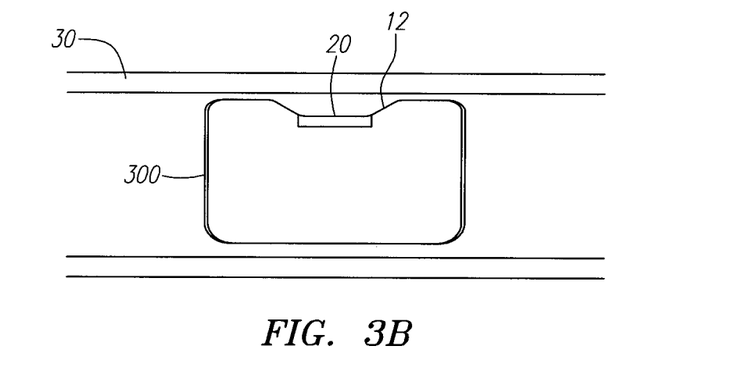
Figure 3C:
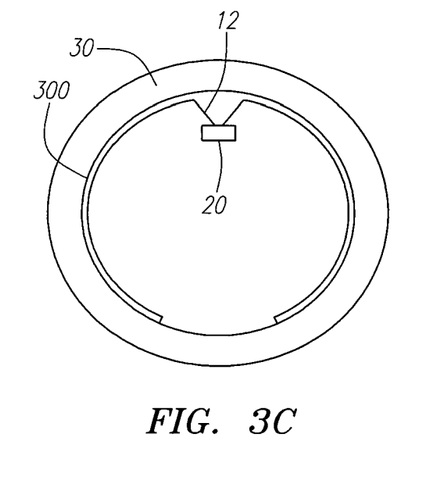

FIG. 3A is a three dimensional view of the device having wing configured fixation element 300 and FIGS. 3B and 3C illustrate longitudinal and lateral cross sections, respectively.

The sensor 20 may be connected to a connecting element 12 for connecting sensor 20 to fixation element 300 and for positioning sensor 20 at a desired location distanced from the lumen wall. In other embodiment sensor 20 can be connected directly to fixation element 300. The sensor can be located between the lumen wall and the center of the lumen. In one embodiment the sensor can be distanced from the lumen wall between 0.05 mm and 0.6r wherein r is the lumen radius. For example, for a blood vessel having radius of r=10 mm the sensor can be positioned at a distance of 0.05 to 8 mm off the vessel wall. However in alternate embodiments, the sensor can be located at any convenient location within the lumen. Additionally, connecting wire 12 can be made of metal such as Nickel-Titanium alloy, stainless steel titanium, cobalt-based alloy, or using tantalum, gold, platinum or platinum-iridium for enhanced radio-opacity, or a polymer including a shape memory polymer with or without the addition of radio-opaque material e.g. barium sulfate, or any known and/or convenient material, made in any convenient shape using any known and/or convenient manufacturing process.

In alternate embodiments, connecting element 12 can be made of metal such as Nickel-Titanium alloy, stainless steel titanium, a polymer or any known and/or convenient material. The connecting element 12 can be rigid so as to maintain sensor 20 at constant position or can be flexible so as to enable movement of the sensor within the lumen. In alternate embodiments, sensor 20 can be connected directly to fixation element 300.

In the embodiments shown in FIGS. 3A-3C, sensor 20 can be oriented parallel, perpendicular or at any other angle to the lumen wall. The active face of the sensor 20 can be oriented towards the lumen center, the lumen wall, tangential to the lumen wall or at any other convenient angle.

Figure 3D:
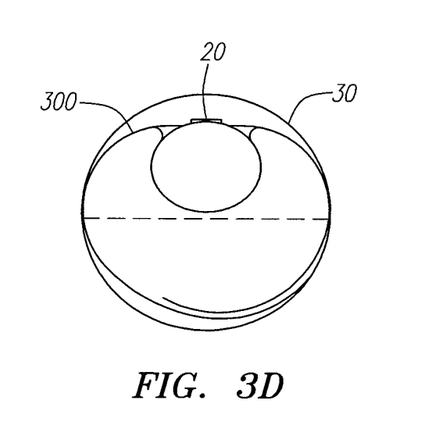

FIG. 3D illustrates a lateral cross section of another configuration of the wing fixation element 300. In the configuration shown in FIG. 3D, the sensor is at the same level as the strut. In those embodiments in which the struts 10 are made of superelastic Nickel-Titanium alloy, intermediate levels of expansion can be implemented such that the predetermined distances of the sensor from the vessel wall can be achieved.

Figure 4A:
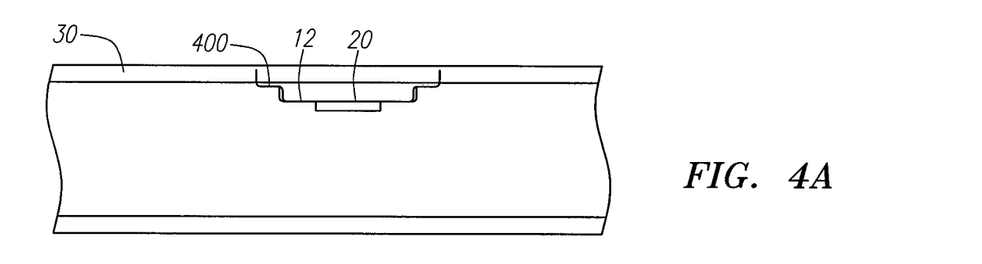
FIGS. 4A-4C are schematic illustrations of a device having a hook configured fixation element according to still another embodiment of the invention.
Figure 4B:
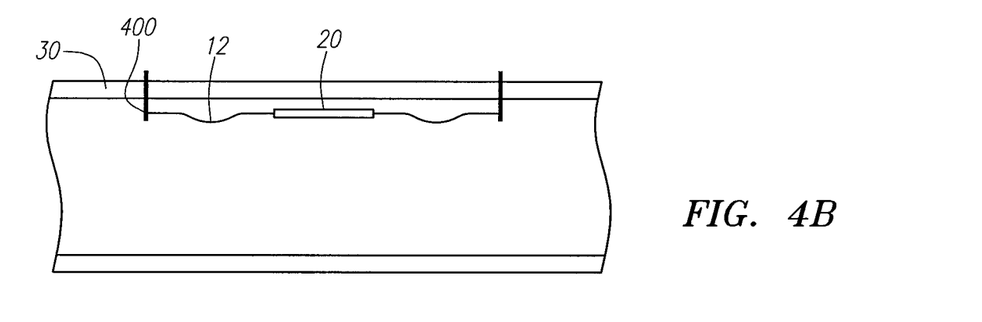
Figure 4C:
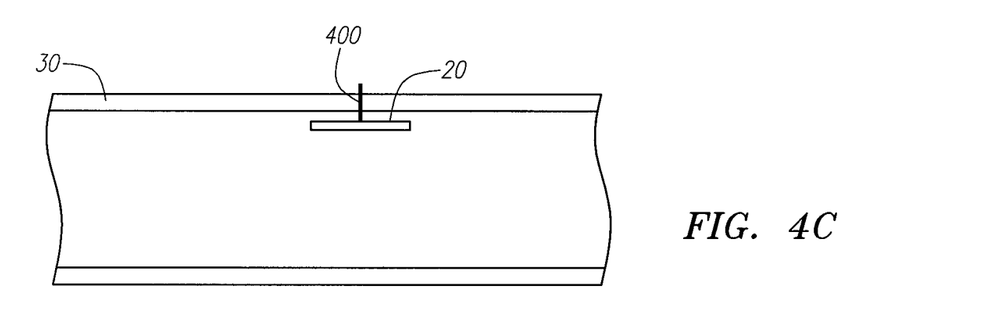

Reference is now made to FIGS. 4A-4C, illustrating a device having a hook configured fixation element according to an embodiment of the invention. The device includes hook configured fixation element 400, connecting element 12 and a sensor 20. Cross section of lumen 30, for example a blood vessel, is shown.

Fixation element 400 can be manufactured from a wire, a laser cut or a chemical etched tube or sheet made of metal, for example Nickel-Titanium alloy, stainless steel titanium, cobalt-based alloy, or a polymer including a shape memory polymer with or without the addition of radio-opaque material e.g. barium sulfate or of any known and/or convenient material, can be manufactured in any convenient shape using any known and/or convenient method of manufacture. The strut of fixation element 400 cross section can be round, oval, rectangular or have any convenient shape. The thickness of struts is in the range of 0.05-1 mm. The struts can have any convenient thickness and/or dimensions. Additionally, the struts can further include ridges or hooks for anchoring fixation element 400 within the lumen and preventing migration within the lumen.

FIG. 4A shows a device having a hook configured fixation element 400 that is hooked into the lumen wall at least at two points. Hooking can be at the longitudinal axis of the lumen as shown in FIG. 4A or at the transverse axis (not shown).

The sensor 20 can be connected to a connecting wire 12, which is configured so as to distance the sensor from the lumen wall. The connecting wire 12 is connected to the fixation element 400. The sensor can be located between the lumen wall and the center of the lumen. In one embodiment the sensor can be distanced from the lumen wall between 0.05 mm and 0.8r wherein r is the lumen radius. For example, for a blood vessel having radius of r=10 mm the sensor can be positioned at a distance of 0.05 to 8 mm of the vessel wall. However in alternate embodiments, the sensor can be located at any convenient location within the lumen.

Connecting element 12 can be made of metal such as Nickel-Titanium alloy, stainless steel titanium, cobalt-based alloy, or using tantalum, gold, platinum or platinum-iridium for enhanced radio-opacity, or a polymer including a shape memory polymer with or without the addition of radio-opaque material e.g. barium sulfate or any known and/or convenient material, can have any convenient shape and can be manufactured using any convenient manufacturing process. Connecting element 12 can be rigid so as to maintain sensor 20 at constant position or can be flexible as illustrated in FIG. 4B, so as to enable movement of the sensor within the lumen. In other embodiment sensor 20 can be connected directly to fixation element 400.

The sensor 20 can be oriented parallel, perpendicular or at any other angle to the lumen wall. The active face of the sensor 20 can be oriented towards the lumen center, the lumen wall, tangential to the lumen wall or at any other convenient angle.

Reference is now made to FIG. 4C, illustrating another configuration of fixation element 400 in which the fixation element 400 is inserted in the lumen similarly to the insertion of a drawing pin. The sensor 20 can be directly connected to fixation element 400 or connected via a connecting wire.

The sensor 20 can be oriented parallel, perpendicular or at any other angle to the lumen wall. The active face of the sensor 20 can be oriented towards the lumen center, the lumen wall, tangential to the lumen wall or any other convenient angle. Additionally, it will be appreciated that other configurations can be used.

Figure 5:
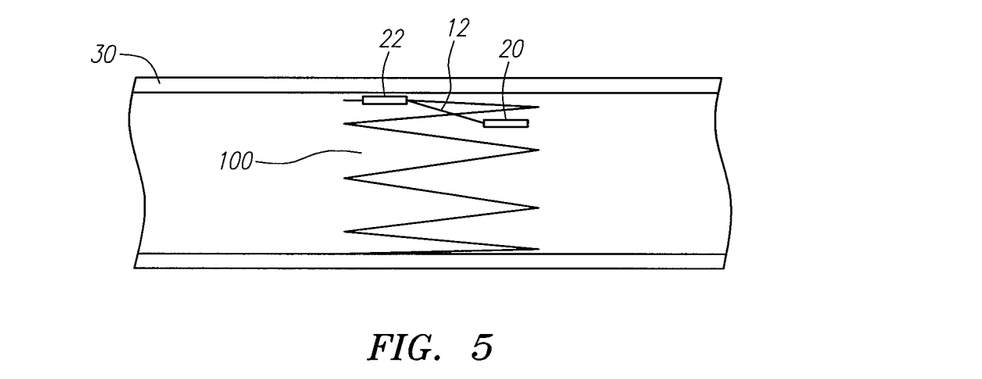
FIG. 5 is a schematic illustration of a device having two implants according to a still further embodiment of the invention.

Reference is now made to FIG. 5 which is a schematic illustration of a device having two implants according to an embodiment of the invention. The device includes a fixation element 100, a first implant 20, a second implant 22, and a connecting element 12. For convenience and clarity, the lumen, which can be a blood vessel, is shown in cross-section.

It will be appreciated that fixation element 100 can have any other configuration such as, for example, coil, wing, hook and/or any other known and or convenient configuration.

A first implant 20 may be located between the lumen wall and the center of the lumen. First implant 20 can be distanced from the lumen wall between 0.05 mm and 0.8r wherein r is the lumen radius. For example, for a blood vessel having radius of r=10 mm the first implant can be positioned at a distance of 0.05 to 8 mm off the vessel wall. Second implant 22 can be in contact with the lumen wall or distanced from the lumen wall. However in alternate embodiments, the first and second implants can be located at any convenient locations within the lumen and relative to each other.

The first implant 20 and second implant 22 may be connected by connecting element 12. Second implant 22 can be directly connected to fixation element 100 or connected through an additional connecting element.

The connecting element 12 may be made of metal such as Nickel-Titanium alloy, stainless steel titanium, cobalt-based alloy, or using tantalum, gold, platinum or platinum-iridium for enhanced radio-opacity, or a polymer including a shape memory polymer with or without the addition of radio-opaque material e.g. barium sulfate, or of any other known and/or convenient material.

The connecting element 12 may be rigid so as to maintain first implant 20 at constant position or can be flexible so as to enable movement of first implant 20 within the lumen. Connecting element 12 that connects first implant 20 to second implant 22 can be a metallic or a plastic tube that includes an electric wire for enabling electric communication between first and second implants. The connection between first implant 20 and second implant 22 can be achieved using mechanical means, crimp, adhesives, welding or any other convenient mechanism and/or material. In alternate embodiments, the connection between the first implant 20 and second implant 22 can be wireless, wired or made in any other known and/or convenient manner. Furthermore, in embodiments in which the second implant 22 is physically connected with the first implant and/or the fixation element 100, the connection element can support both the first implant and the second implant. Alternately, each implant can have a separate connection element 12 to connect the implant with the fixation element.

In one embodiment first implant 20 can be a sensor such as pressure sensor and second implant 22 can be an energy source such as a battery. The sensor and the battery can be connected by electric wire for enabling energy transfer from the battery to the sensor.

While the invention is susceptible to various modifications, and alternative forms, specific examples thereof have been shown in the drawings and are herein described in detail. It should be understood, however, that the invention is not to be limited to the particular embodiments or methods disclosed, but to the contrary, the invention is to cover all modifications, equivalents, and alternatives falling within the scope of the appended claims.

What is claimed is:

1. An implantable vascular pressure sensor for sensing blood pressure within a pulmonary artery, the sensor comprising:
   a sensor configured to sense blood pressure within the pulmonary artery; and
   a fixation element configured to secure the sensor to a wall of the pulmonary artery, wherein, when the fixation element is disposed within the pulmonary artery, the sensor is located between the wall of the pulmonary artery and a center of the pulmonary artery, the fixation element including:
      a first wire loop having a first section fixedly attached to, and extending away from, a first portion of the sensor, the first wire loop having a second section making at least one turn, and the first wire loop having a third section returning to the sensor at, and fixedly attached to, a second portion of the sensor different from the first portion, wherein at least a part of each of the first and third sections of the first wire loop is disposed in a first plane, and at least a part of the second section of the first wire loop is disposed in a second plane that intersects the first plane, the first wire loop comprised entirely of a first wire configured to expand from a collapsed position to an expanded position within the pulmonary artery, wherein, in the expanded position of the first wire loop, an outer periphery of the first wire loop is configured to contact and assert a radial force against the wall at a first location within the pulmonary artery; and
      a second wire loop having a first section fixedly attached to, and extending away from, a third portion of the sensor different from the first and second portions, the second wire loop having a second section making at least one turn, and the second wire loop having a third section returning to the sensor at, and fixedly attached to, a fourth portion of the sensor different from the first, second, and third portions, wherein at least a part of each of the first and third sections of the second wire loop is disposed in a third plane, and at least a part of the second section of the second wire loop is disposed in a fourth plane that intersects the third plane, the second wire loop comprised entirely of a second wire configured to expand from a collapsed position to an expanded position within the pulmonary artery, wherein, in the expanded position of the second wire loop, an outer periphery of the second wire loop is configured to contact and assert a radial force against the wall at a second location within the pulmonary artery.

2. The pressure sensor of claim 1, wherein the sensor is laterally offset from the outer periphery of the first and second wire loops such that, in the expanded position, the sensor is located radially inward and spaced a distance apart from the wall of the pulmonary artery.

3. The pressure sensor of claim 1, wherein, when the fixation element is disposed within the pulmonary artery, the sensor is located less than approximately 0.8r away from the wall, wherein r represents the artery radius.

4. The pressure sensor of claim 1, wherein the first and second wire loops each comprise a single wire loop.

5. The pressure sensor of claim 1, further comprising a first connecting element connecting the first wire loop to the sensor and a second connecting element connecting the second wire loop to the sensor.

6. The pressure sensor of claim 5, wherein the first and second connecting elements are wires.

7. The pressure sensor of claim 5, wherein the first and second connecting elements are flexible.

8. The pressure sensor of claim 5, wherein the first and second connecting elements are rigid.

9. The pressure sensor of claim 1, wherein an active face of the sensor is adapted to be oriented towards a center of the pulmonary artery.

10. The pressure sensor of claim 9, wherein the active face of the sensor is adapted to be oriented parallel to the wall of the pulmonary artery.

11. The pressure sensor of claim 9, wherein the first and second wire loops are coupled to the sensor on a side opposite the active face.

12. The pressure sensor of claim 9, wherein the active face of the sensor is laterally offset from the outer periphery of the first and second wire loops.

13. The pressure sensor of claim 9, wherein the active face of the sensor is laterally aligned with the outer periphery of the first and second wire loops.

14. The pressure sensor of claim 1, wherein the first and second wire loops are formed at least in part of a metal.

15. The pressure sensor of claim 14, wherein the metal includes a nickel-titanium alloy.

16. The pressure sensor of claim 1, wherein the first and second wire loops are formed at least in part of a polymer.

17. The pressure sensor of claim 1, wherein the sensor includes an energy storage device.

18. An implantable vascular pressure sensor for sensing blood pressure within a pulmonary artery, the sensor comprising:
a sensor configured to sense blood pressure within the pulmonary artery; and
a fixation element configured to secure the sensor to a wall of the pulmonary artery, wherein, when the fixation element is disposed within the pulmonary artery, the sensor is located between the wall of the pulmonary artery and a center of the pulmonary artery, the fixation element including:
a first wire loop having a first section fixedly attached to, and extending away from, a first portion of the sensor, the first wire loop having a second section making at least one turn, and the first wire loop having a third section returning to the sensor at, and fixedly attached to, a second portion of the sensor different from the first portion, wherein at least a part of each of the first and third sections of the first wire loop is disposed in a first plane, and at least a part of the second section of the first wire loop is disposed in a second plane that intersects the first plane, and extending at least in part proximally from the sensor along a longitudinal axis of the pulmonary artery, the first wire loop comprised entirely of a first wire configured to expand from a collapsed position to an expanded position within the pulmonary artery, wherein, in the expanded position of the first wire loop, an outer periphery of the first wire loop is configured to contact and assert a radial force against the wall at a first location within the pulmonary artery proximal to the sensor;
a second wire loop having a first section fixedly attached to, and extending away from, a third portion of the sensor different from the first and second portions, the second wire loop having a second section making at least one turn, and the second wire loop having a third section returning to the sensor at, and fixedly attached to, a fourth portion of the sensor different from the first, second, and third portions, wherein at least a part of each of the first and third sections of the second wire loop is disposed in a third plane, and at least a part of the second section of the second wire loop is disposed in a fourth plane that intersects the third plane, and extending at least in part distally from the sensor along the longitudinal axis of the pulmonary artery, the second wire loop comprised entirely of a second wire configured to expand from a collapsed position to an expanded position within the pulmonary artery, wherein, in the expanded position of the second wire loop, an outer periphery of the second wire loop is configured to contact and assert a radial force against the wall at a second location within the pulmonary artery distal to the sensor.

19. An implantable vascular pressure sensor for sensing blood pressure within a pulmonary artery, the sensor comprising:
a sensor configured to sense blood pressure within the pulmonary artery; and
a fixation element configured to secure the sensor to a wall of the pulmonary artery, wherein, when the fixation element is disposed within the pulmonary artery, the sensor is located between the wall of the pulmonary artery and a center of the pulmonary artery, the fixation element including:
a first anchoring member having a first section fixedly attached to, and extending away from, a first portion of the sensor, the first anchoring member having a second section making at least one turn, and the first anchoring member having a third section returning to the sensor at, and fixedly attached to, a second portion of the sensor different from the first portion, wherein at least a part of each of the first and third sections of the first anchoring member is disposed in a first plane, and at least a part of the second section of the first anchoring member is disposed in a second plane that intersects the first plane, the first anchoring member comprising a single wire loop formed entirely of a first wire configured to expand from a collapsed position to an expanded position within the pulmonary artery, wherein, in the expanded position, an outer periphery of the first anchoring member is configured to contact and assert a radial force against the wall at a first location within the pulmonary artery;
a second anchoring member having a first section fixedly attached to, and extending away from, a third portion of the sensor different from the first and second portions, the second anchoring member having a second section making at least one turn, and the second anchoring member having a third section returning to the sensor at, and fixedly attached to, a fourth portion of the sensor different from the first, second, and third portions, wherein at least a part of each of the first and third sections of the second anchoring member is disposed in a third plane, and at least a part of the second section of the second anchoring member is disposed in a fourth plane that intersects the third plane, the second anchoring member comprising a single wire loop formed entirely of a second wire configured to expand from a collapsed position to an expanded position within the pulmonary artery, wherein, in the expanded position, an outer periphery of the second anchoring member is configured to contact and assert a radial force against the wall at a second location within the pulmonary artery.

* * * * *